US012453839B2

(12) United States Patent
Dale et al.

(10) Patent No.: US 12,453,839 B2
(45) Date of Patent: Oct. 28, 2025

(54) DELIVERY DEVICES AND METHODS FOR RIGHT HEART ACCESS

(71) Applicant: St. Jude Medical, Cardiology Division, Inc., St. Paul, MN (US)

(72) Inventors: Theodore Paul Dale, Corcoran, MN (US); Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 327 days.

(21) Appl. No.: 18/323,687

(22) Filed: May 25, 2023

(65) Prior Publication Data

US 2024/0050700 A1 Feb. 15, 2024

Related U.S. Application Data

(60) Provisional application No. 63/371,505, filed on Aug. 15, 2022.

(51) Int. Cl.

| | |
|---|---|
| ***A61M 25/01*** | (2006.01) |
| ***A61B 17/00*** | (2006.01) |
| ***A61M 25/09*** | (2006.01) |
| ***A61M 29/00*** | (2006.01) |

(52) U.S. Cl.
CPC ..... *A61M 25/0147* (2013.01); *A61B 17/0057* (2013.01); *A61M 25/09* (2013.01); *A61M 29/00* (2013.01); *A61B 2017/00526* (2013.01); *A61B 2017/00606* (2013.01); *A61M 2207/10* (2013.01)

(58) Field of Classification Search
CPC .. A61M 25/09; A61M 25/0147; A61M 29/00; A61B 17/00; A61B 17/0057; A61B 17/12022; A61B 17/12027; A61B 17/12131; A61B 17/12099; A61B 2017/00526
See application file for complete search history.

(56) References Cited

U.S. PATENT DOCUMENTS

2004/0049207 A1* 3/2004 Goldfarb ............ A61B 17/1227 606/139
2006/0252984 A1* 11/2006 Rahdert ............. A61B 17/0401 623/2.37
2011/0245800 A1 10/2011 Kassab
2015/0045696 A1 2/2015 Osypka
2019/0167305 A1 6/2019 Pedersen

* cited by examiner

*Primary Examiner* — Vi X Nguyen
(74) *Attorney, Agent, or Firm* — SLEMAN & LUND LLP

(57) ABSTRACT

According to one aspect of the disclosure, a method of advancing a delivery catheter to a heart of a patient includes advancing a guidewire through the vasculature of the patient until the guidewire reaches a target treatment site in or adjacent to the heart. A dilator may be positioned within the delivery catheter so that a distal tip of the dilator extends beyond a distal end of the delivery catheter. The dilator may be advanced through the vasculature of the patient directly over the guidewire while simultaneously advancing the delivery catheter through the vasculature until the distal tip of the dilator reaches the target treatment site. While maintaining the distal tip of the dilator substantially stationary relative to the target treatment site, the delivery catheter may be advanced over the dilator until the distal end of the delivery catheter is positioned at the target treatment site.

16 Claims, 16 Drawing Sheets

DELIVERY DEVICES AND METHODS FOR RIGHT HEART ACCESS

CROSS-REFERENCE TO RELATED APPLICATIONS

This application claims the benefit of the filing date of U.S. Provisional Patent Application No. 63/371,505, filed Aug. 15, 2022, the disclosure of which is hereby incorporated by reference herein.

BACKGROUND OF THE DISCLOSURE

Various medical devices and implants are configured to be delivered to the heart or adjacent the heart via minimally invasive transcatheter delivery. For example, various self-expandable occluders are configured to be collapsed within a delivery device and advanced to a defect in or adjacent the heart, with the occluder self-expanding into the defect upon being released from the delivery device. Similarly, pressure sensing devices are configured for implantation within vessels leading to or from the heart, such as a pulmonary artery trunk. These devices may be positioned within or coupled to catheters that are advanced from a patient's groin all the way to vessels branching from the pulmonary artery. Such delivery methods may require a significant number of steps with multiple guidewires and catheters being inserted and switched out for larger or stiffer members until the final delivery catheter is ready to be advanced to the target site. Furthermore, it may be desirable for such delivery systems to have steering capabilities due to the relatively tortuous pathway that the delivery device must traverse to reach the target site. However, prior art delivery devices that have steering capability typically have smaller payload capabilities compared to identical delivery devices without a steering capability. Despite this, it would be preferable to maintain steering capabilities while maximizing catheter payload, and it would also be preferable to reduce the number of steps required for the final delivery catheter to reach the target site.

BRIEF SUMMARY OF THE DISCLOSURE

According to one aspect of the disclosure, a method of advancing a delivery catheter to a heart of a patient includes advancing a guidewire through the vasculature of the patient until the guidewire reaches a target treatment site in or adjacent to the heart. A dilator may be positioned within the delivery catheter so that a distal tip of the dilator extends beyond a distal end of the delivery catheter. The dilator may be advanced through the vasculature of the patient directly over the guidewire while simultaneously advancing the delivery catheter through the vasculature until the distal tip of the dilator reaches the target treatment site. While maintaining the distal tip of the dilator substantially stationary relative to the target treatment site, the delivery catheter may be advanced over the dilator until the distal end of the delivery catheter is positioned at the target treatment site. The treatment site may be a patent ductus arteriosus or a left pulmonary trunk. The guidewire may have a diameter of about 0.014 inches (about 0.35 mm). The delivery device may have an inner diameter of about 4 French (about 1.33 mm). When the distal tip of the dilator reaches the target treatment site, the distal end of the catheter may be spaced from the distal tip of the dilator by a distance of between about 3 cm and about 15 cm. When the distal tip of the dilator reaches the target treatment site, the distal end of the catheter may remain outside of the heart.

According to another aspect of the disclosure, a delivery system is described for delivering a medical device to a target site in a patient within or adjacent a heart of the patient. The delivery system may include a delivery catheter defining a lumen therethrough and having an open distal end, and a dilator having a tapered distal tip and an outer diameter sized to fit within the lumen of the delivery catheter. The dilator may include a steering ring coupled to a distal end portion of the dilator, at least one pull wire or steering cable being coupled to the steering ring and extending through a wall of the dilator to a steering mechanism operably coupled to the dilator. The terms "pull wire" and "steering cable" are used interchangeably herein and have the same meaning. The delivery catheter may exclude any steering cables extending through a wall of the delivery catheter. The dilator may include a central guidewire lumen extending therethrough, the central guidewire lumen opening to the tapered distal tip of the dilator. The dilator may include a plurality of peripheral steering cable lumens positioned radially outward of the central guidewire lumen, the at least one pull wire extending through a corresponding one of the plurality of steering cable lumens.

According to a further embodiment of the disclosure, a method of manufacturing a dilator for use with a delivery catheter includes forming the dilator to have a cylindrical base and a central guidewire lumen extending through the cylindrical base. A steering ring may be positioned over a distal end portion of the cylindrical base, the steering ring having at least one steering cable coupled thereto. After positioning the steering ring, an exterior jacket may be formed over the cylindrical base so that the exterior jacket has a proximal portion formed of a first material and a distal portion formed of a second material different than the first material, the proximal portion being stiffer than the distal portion. The proximal portion may be positioned proximal to the steering ring, and the distal portion may be positioned distal to the steering ring. The proximal portion may directly transition to the distal portion. Forming the exterior jacket may include forming an intermediate portion between the proximal portion and the distal portion, the intermediate portion being formed of both the first material and the second material so that the intermediate portion is stiffer than the distal portion, and the proximal portion is stiffer than the intermediate portion. The cylindrical base, upon being formed, may include a channel extending longitudinally along an outer surface of the cylindrical base. Positioning the steering ring over the distal end portion of the cylindrical base may include positioning the steering ring at a distal end of the channel so that the at least one steering cable extends along the channel.

According to another embodiment of the disclosure, a method of manufacturing a dilator for use with a delivery catheter includes forming the dilator to have (i) a cylindrical body extending to a tapered distal tip, (ii) a central guidewire lumen extending through the dilator, and (iii) at least one peripheral steering lumen positioned radially outside of the central guidewire lumen. An annular groove may be formed in a distal end portion of the cylindrical body by compressing and heating the distal end portion of the cylindrical body. A steering ring may be positioned within the annular groove and the steering ring may be coupled to the dilator. A steering cable may be coupled to the steering ring, with the steering cable extending through the at least one peripheral steering lumen. A tube may be positioned over the steering ring so that the tube extends beyond both ends of the annular groove. The tube may be heated to thermally reflow the tube.

Forming the dilator to have the tapered distal tip may include heat shaping the distal end of the cylindrical body to have an ogive shape.

DETAILED DESCRIPTION OF THE INVENTION

As used herein, the term “proximal,” when used in connection with a delivery device or system, refers to a direction relatively close to the user of that device or system when being used as intended, while the term “distal” refers to a direction relatively far from the user of the device. In other words, the leading end of a delivery device or system is positioned distal to the trailing end of the delivery device or system, when being used as intended. As used herein, the terms “substantially,” “generally,” “approximately,” and “about” are intended to mean that slight deviations from absolute are included within the scope of the term so modified.

Figure 1:
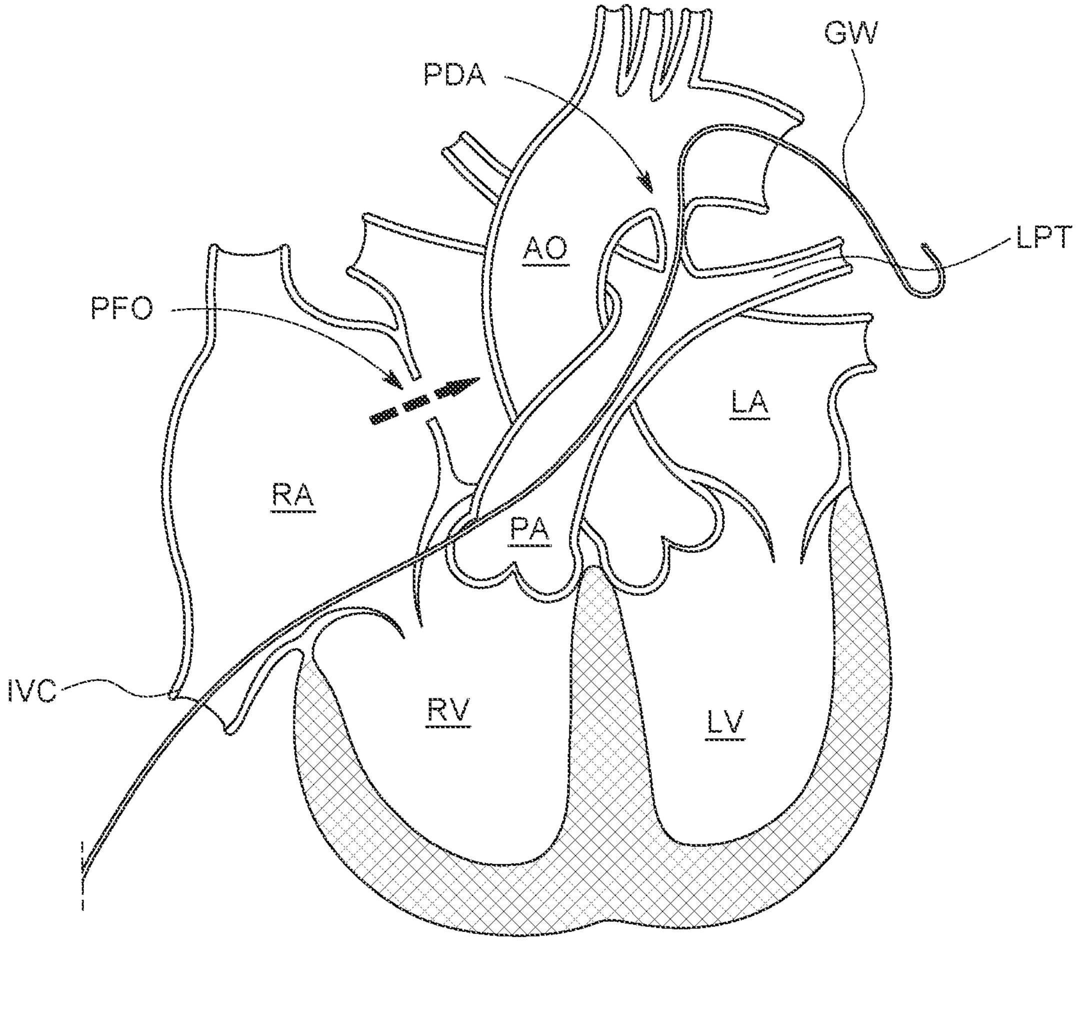
FIG. 1 is a highly schematic cross-section of a human heart with a guidewire extending into a patent ductus arteriosus.

FIG. 1 is a cross-section of a human heart illustrating a guidewire GW having been delivered to a treatment site within the heart. The human heart of FIG. 1 includes at least two illustrated defects, including a patent foramen ovale (“PFO”), which is a small opening between the right atrium RA and the left atrium LA, and a patent ductus arteriosus (“PDA”), which is an opening between the pulmonary artery PA and the aorta AO. Various treatment procedures in or adjacent to the human heart require a delivery device to access the heart or adjacent structures, including via trans-catheter delivery through the right heart. The guidewire GW in FIG. 1 has passed through the inferior vena cava IVC into the right atrium RA (after being introduced through the femoral vein, not shown), through the tricuspid valve into the right ventricle RV, through the pulmonary valve into the pulmonary artery PA, and across the patent ductus arteriosus PDA into the descending trunk of the aorta AO. Although the guidewire in FIG. 1 is illustrated as crossing over tissue between the right atrium RA and the pulmonary artery PA, it should be understood that in practice, the guidewire GW would follow the pathway described above. This may be a typical pathway for treating patent ductus arteriosus PDA, which may include implanting a self-expanding occlusion device, for example, the Amplatzer™ Duct Occluder or the Amplatzer Piccolo™ Occluder, both offered by Abbott Laboratories. It should be understood that the devices and concepts described herein may work from other access points (besides the femoral vein) such as the jugular vein (which will result in traversing the superior vena cava SVC instead of the inferior vena cava IVC). Other minimally invasive medical devices may be implanted using delivery catheters that traverse a similar pathway. For example, Abbott Laboratories offers a CardioMEMS™ HF System which is implanted into the pulmonary artery PA and used for remote monitoring of pulmonary artery PA pressure. The CardioMEMS™ HF System may be delivered through a similar route as shown in FIG. 1, but instead of passing through a patent ductus arteriosus PDA (which is a defect that may not exist in a patient receiving the CardioMEMS™ HF System), the pathway extends from the pulmonary artery PA into the left pulmonary trunk LPT where the device is implanted for remote pressure monitoring. For these and other medical devices, the device is typically contained within or connected to a catheter that is passed through the vasculature while the heart remains beating.

For procedures such as implanting an Amplatzer Piccolo™ Occluder or a CardioMEMS™ HF System device, there are typically numerous guidewires and catheters that need to be sequentially inserted or withdrawn from the patient before the delivery device containing the medical implant is ready for being advanced to the target site. For example, because of the distance that the delivery devices need to travel, as well as the tortuosity of the vascular pathways, a highly flexible, small diameter guidewire is typically required to establish the initial pathway to the target site. However, this initial guidewire may be too flexible (i.e., not stiff enough) for the relatively stiff delivery device that houses (or is connected to) the medical device to directly ride over that initial guidewire. In other words, if the delivery device has a stiffness that is too great compared to the guidewire, the guidewire may not be able to support the delivery device along the desired pathway. Thus, a microcatheter is often used to ride over the initial guidewire until the microcatheter reaches the treatment site. Then, the initial guidewire is removed from the patient, and another stiffer guidewire is passed through the microcatheter, with the microcatheter guiding the stiffer guidewire to the treatment site. An alternative to using a microcatheter is to use a Swans-Ganz catheter (“SGC”) that has a small balloon, is inflated, and due to the flow of blood, the balloon floats with the blood up through the pulmonic valve and into the pulmonary arteries. The SCG is capable of wire exchanges. Once the stiffer guidewire reaches the treatment site, the delivery catheter may be passed over the stiff guidewire, with the stiffer guidewire being able to support the delivery catheter as the delivery catheter rides over the stiff guidewire to the treatment site. Finally, the stiffer guidewire may be removed, and the medical device passed through the delivery catheter to the treatment site.

Figure 2:
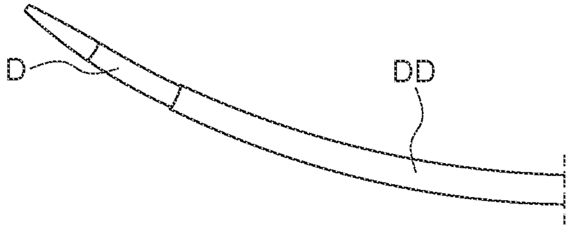
FIG. 2 (Prior Art)
FIG. 2 is a perspective view of a delivery device and a dilator positioned within the delivery device, according to the prior art.

A specific example of the current state of accessing and treating a patent ductus arteriosus PDA is provided below. First, the patient's femoral vein may be accessed and a first guidewire GW, for example with a diameter of about 0.014 inches (about 0.35 mm), may be advanced in an antegrade direction along the femoral vein, into the right atrium RA via the inferior vena cava IVC, across the tricuspid valve into the right ventricle RV, through the pulmonary valve into the pulmonary artery PA, through the patent ductus arteriosus PDA, and a short distance into the descending portion of the aorta AO. This results in the configuration shown in FIG. 1. The high flexibility of a 0.014 inch (about 0.35 mm) guidewire GW may help navigate the curves and bends required to reach the final positioning shown in FIG. 1. However, as noted above, the actual delivery device used to deliver the occluder may be too stiff to be able to reliably ride over the small flexible guidewire to reach the target site. Thus, after the first guidewire GW is positioned in place, a microcatheter (not shown) may be passed over the 0.014 inch (about 0.35 mm) until the microcatheter crosses the patent ductus arteriosus PDA. Microcatheters are generally thought of as any catheter having a diameter of about 2.5 French (0.083 mm) or smaller. Microcatheters may be formed of various suitable materials, including a polyether block amide offered under the tradename PEBAX®, nylon, layered polytetrafluoroethylene ("PTFE") liner with a polymer jacket, liners having a braided construction and jackets formed of braided polymer. However these materials are merely exemplary. With the microcatheter in place, the first guidewire GW may be removed from the patient through the microcatheter, and a second guidewire GW with a diameter of between about 0.025 inches (about 0.635 mm) and about 0.035 inches (about 0.89 mm) may be advanced through the interior of the microcatheter until the second guidewire GW crosses the patent ductus arteriosus PDA. The main difference between the first guidewire GW and the second guidewire GW is the diameter. Otherwise, the first and second guidewire GW may have a similar construction, for example with a spring tip and a stiffer proximal section proximal to the spring tip. Then, the microcatheter may be removed from the patient, the microcatheter riding over the second guidewire GW in the process. At this point, again the configuration of FIG. 1 is achieved, only with a second guidewire GW that is larger in diameter (and thus stiffer) than the first guidewire GW. With the second, stiffer guidewire GW in place, the occluder delivery device DD may be advanced over the second, stiff guidewire GW. The delivery device DD, shown in FIG. 2, may be a catheter having an inner diameter size of about 4 French (about 1.33 mm). When advancing the delivery device DD over the second guidewire GW, a dilator D is positioned within and through the delivery device DD, with a small length (for example typically between about 1 cm and about 3 cm) of the dilator D extending beyond the distal end of the delivery device DD, the small length including a tapered tip in order to help smoothly pass the delivery device DD through the vasculature while riding over the second guidewire GW. Once the dilator D passes into or through the patent ductus arteriosus PDA, the delivery device DD is advanced over the dilator D and into the ostium of the patent ductus arteriosus PDA and the dilator D and second guidewire GW may be removed from the patient through the delivery device DD (either simultaneously or one after the other in either sequence), leaving only the delivery device DD within the patient. At this point, the occluder device, which may be coupled (e.g., threaded) onto a distal end of a delivery cable, may be advanced through the delivery device DD while in a collapsed condition until the occluder reaches the distal end of the delivery device DD. The occluder may be passed through the open distal end of the delivery device DD (by retracting the delivery device DD proximally, advancing the occluder distally, or both), resulting in the occluder self-expanding within the patent ductus arteriosus PDA. With the desired positioning of the occluder relative to the patent ductus arteriosus PDA confirmed, the delivery cable may be disconnected from the expanded occluder, for example by rotating the delivery cable to unthread the delivery cable from the expanded occluder. At this point, the delivery cable and delivery device DD may be removed from the patient, either simultaneously or in either sequence.

Figure 3:
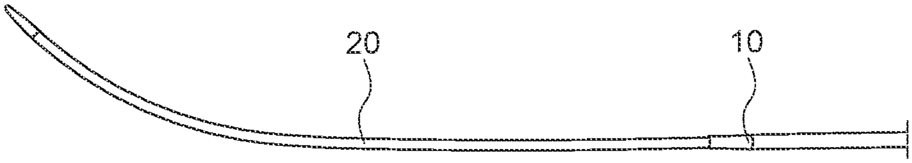
FIG. 3 is a perspective view of a delivery device and an extended dilator positioned within the delivery device, according to an aspect of the disclosure.

According to one aspect of the disclosure, a delivery device 10, as shown in FIG. 3, may be similar to delivery device DD, with the exception that the dilator 20 used with the delivery device 10 extends a distance (for example between about 5 cm and about 15 cm) beyond the distal end of the delivery device 10 a distance that is significantly larger than that of dilator D. For example, whereas dilator D may have an exposed length of up to about 3 cm, dilator 20 may have an exposed length of about 1 cm to about 15 cm. Preferably, the exposed length of dilator 20 is between about 3 cm and about 15 cm, including between about 5 cm and about 10 cm. The extended dilator 20, compared to the standard dilator D, may allow for a number of delivery steps to be eliminated, resulting in a faster and more efficient procedure. An example of a more efficient delivery is described below.

Figure 4:
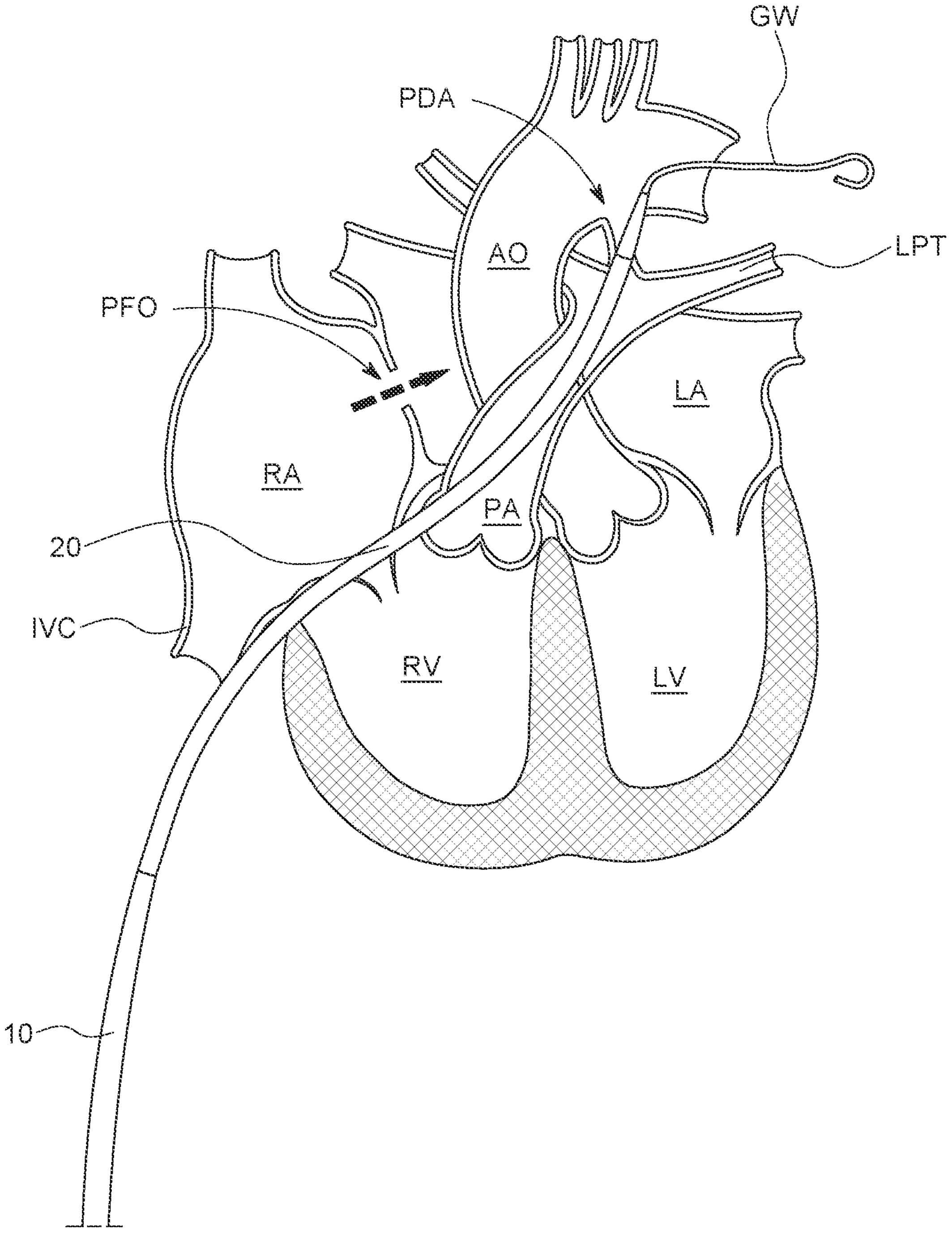
FIGS. 4-7 are schematic illustrations of the delivery device and dilator of FIG. 3 at different stages of delivery to a patent ductus arteriosus.

A procedure to deliver a patent ductus arteriosus PDA occluder may begin identically as described above, with a highly flexible guidewire GW, for example having a diameter of about 0.014 inches (about 0.35 mm), may be delivered in the same manner as described above resulting in the positioning shown in FIG. 1. The delivery device 10 may be too stiff to directly thread over the small diameter guidewire GW, but by extending the dilator 20 a greater distance beyond the delivery device 10, the dilator 20 may act similarly to the microcatheter described above. For example, the dilator may be flexible enough to ride over the small diameter guidewire GW while being sufficiently supported by the small diameter guidewire GW. The extended length of the dilator 20 eliminates the need to use a microcatheter to switch out the small diameter guidewire GW with a large diameter guidewire, reducing the complexity and the length of the procedure. For example, the dilator 20 may be formed of a lower durometer, softer material than the delivery device 10. The protruding length of the dilator 20 may more easily ride over the guidewire GW without significantly affecting the position of the guidewire GW because of how soft the dilator 20 is. The portions of the dilator 20 overlying the guidewire GW create a significantly higher bending moment of inertia compared to that of the guidewire GW alone, as the moment of inertia of a circle is based on a quartic relationship (e.g. diameter to the fourth power). In other words, the extended portion of the dilator 20 is able to easily bend over the guidewire GW, but the combined guidewire GW and dilator 20 provide enough stiffness for the delivery device 10 to ride over. As shown in FIG. 4, the small diameter guidewire GW may remain in place as the delivery device 10 and the dilator 20 positioned within the delivery device 10 are advanced along the small diameter guidewire GW. Similar to FIG. 1, although the dilator 20 is illustrated in FIGS. 4-7 as crossing over tissue between the right atrium RA and the pulmonary artery PA, it should be understood that in practice, the dilator 20 would follow the pathway of the guidewire GW described above. The dilator 20 may have enough length that, when the tapered distal tip of the dilator 20 is within or adjacent to the patent ductus arteriosus PDA, the distal end of the delivery device 10 is still outside the heart (e.g., within the inferior vena cava IVC). Once the tip of the dilator 20 is at the target site, the dilator 20 may be fixed relative to the patient (e.g., by manually pinning or holding it to the operating table) to restrict further movement of the dilator 20.

Figure 5:
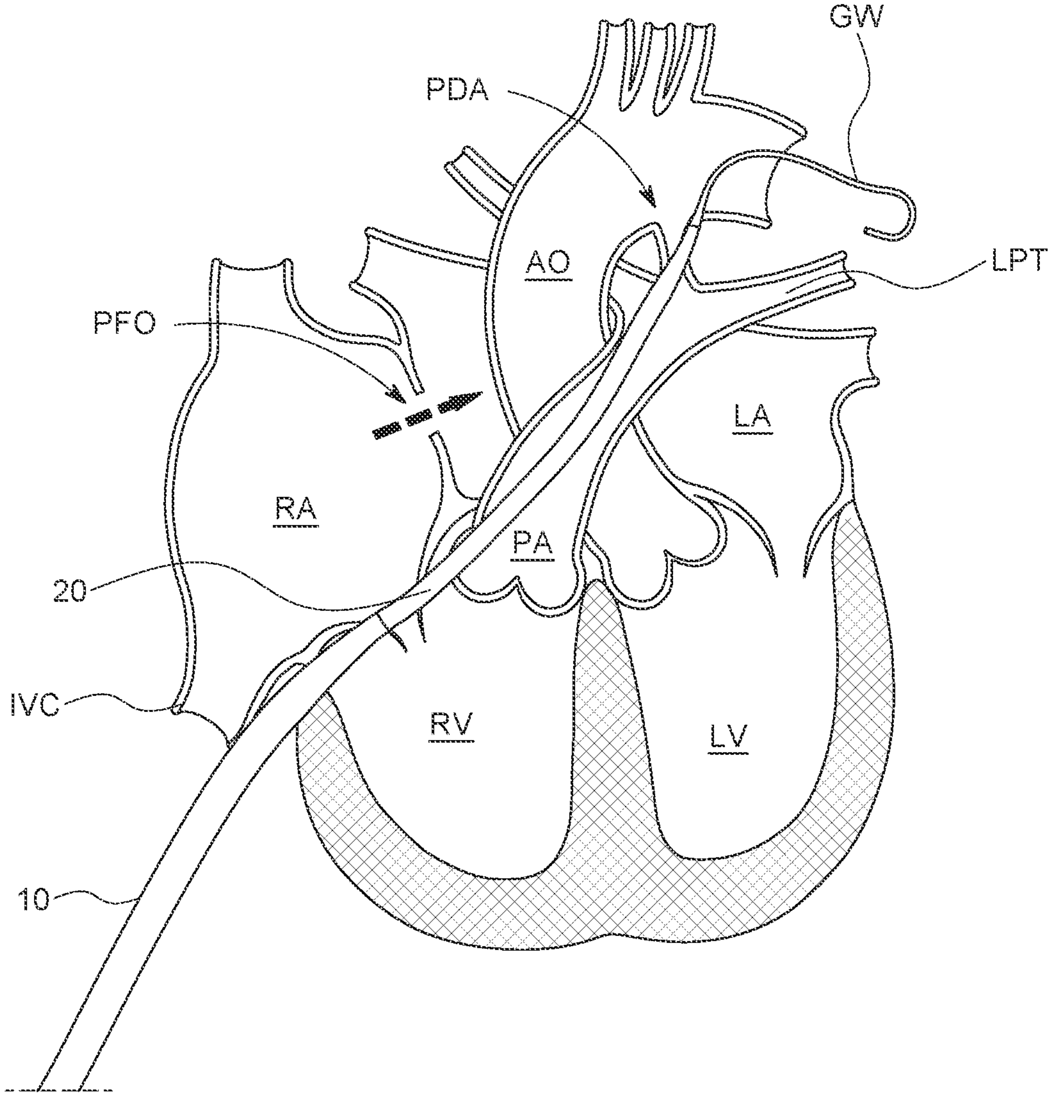
Figure 6:
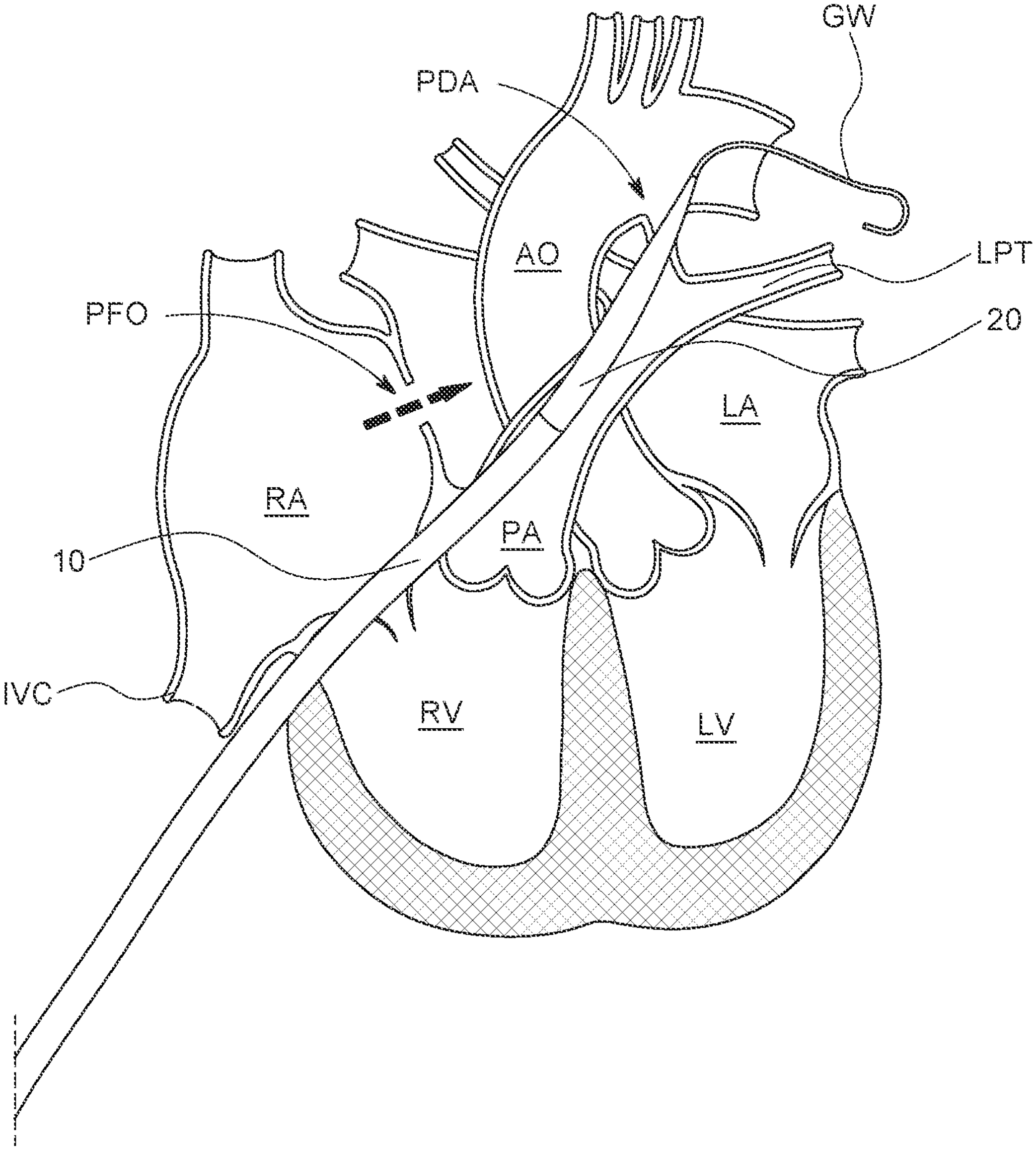
Figure 7:
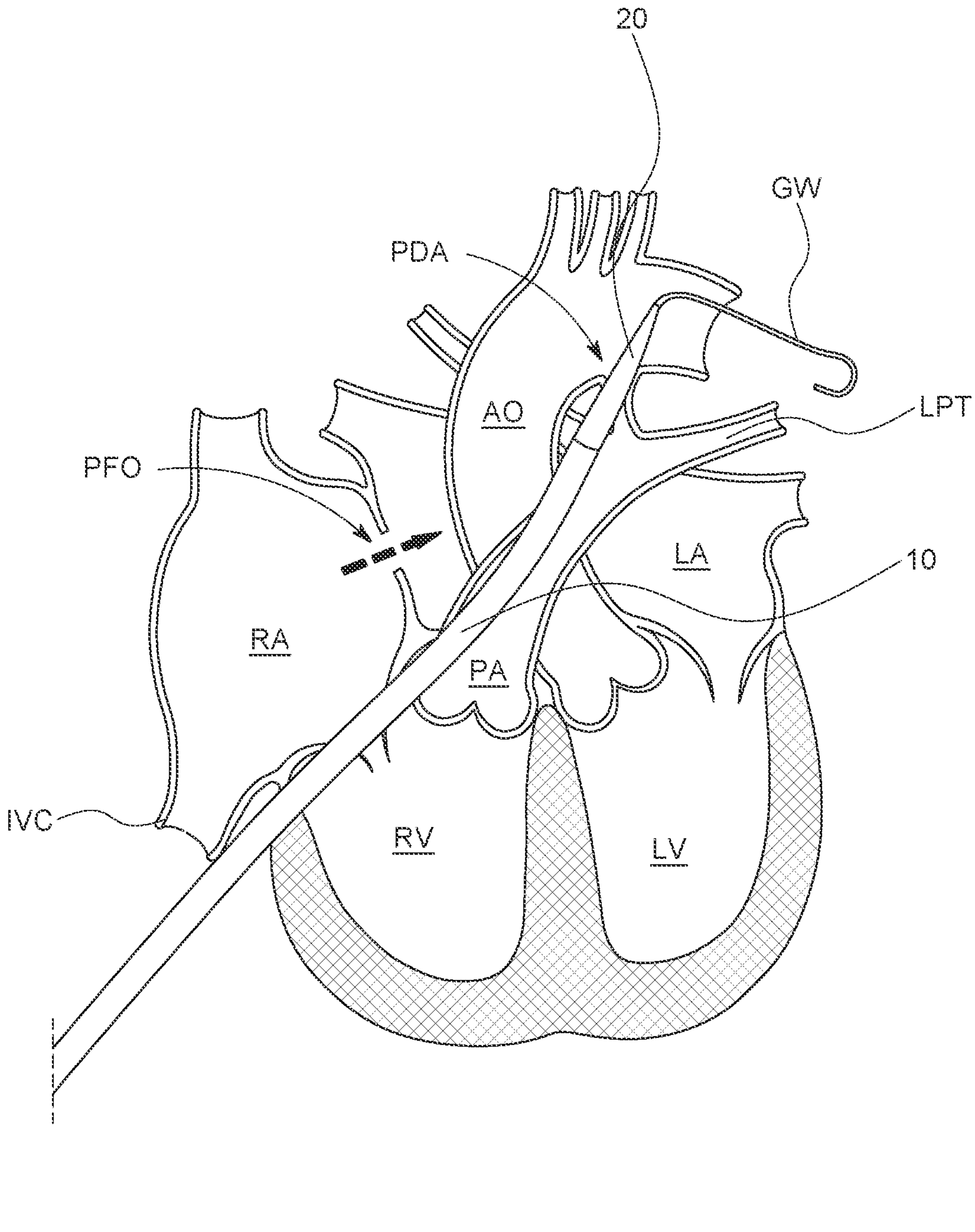
Figure 8:
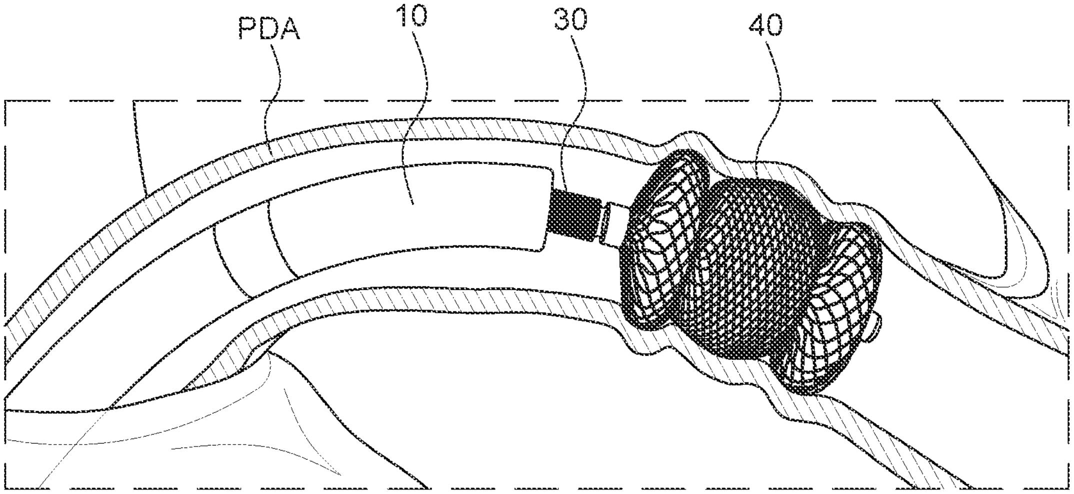
FIG. 8 illustrates the delivery device of FIGS. 4-7 after being withdrawn to deploy an occluder within the patent ductus arteriosus.

Once the dilator 20 is locked in position, as shown in FIG. 4, the delivery device 10 may be advanced distally over the dilator 20. As shown in the sequence of FIGS. 5-7, the delivery device 10 is advanced distally into the right atrium RA, across the tricuspid valve into the right ventricle RV, across the pulmonary valve into the pulmonary artery PA, and eventually into or adjacent to the patent ductus arteriosus PDA, as shown in FIG. 7, all while the dilator 20 remains substantially stationary relative to the patient's anatomy. Once the distal end of the delivery device 10 is at the desired position at the target site, the small diameter guidewire GW and dilator 20 may be withdrawn proximally through the delivery device 10 (simultaneously or in either sequence) and out of the patient. From this point, the delivery of the occluder 40 may be substantially the same as described above in connection with the current state of the art. For example, as shown in FIG. 8, the occluder 40 may be coupled to a delivery cable 30 that is passed through the delivery device 10 while the occluder 40 is in a collapsed condition. Then, with the occluder 40 at the distal end of the delivery device 10, the delivery device 10 may be withdrawn proximally as the delivery cable 30 remains stationary. As the occluder 40 clears the delivery device, it self-expands into the patent ductus arteriosus PDA to begin to occlude blood flow between the pulmonary artery PA and the aorta AO. Once deployed in the desired position, the delivery cable 30 may be rotated to disconnect it from the occluder 40, and the delivery cable 30 and delivery device 10 may be withdrawn from the patient (simultaneously or in either sequence) to complete the procedure.

Although the extended dilator 20 is described in connection with the implantation of an occluder 40 to occlude a patent ductus arteriosus, it should be understood that the extended dilator 20 may be used with delivery device 10 (or similar delivery devices) to implant other medical devices in a faster and/or more efficient method than has been done previously. For example, other expandable occluders such as PFO or left atrial appendage ("LAA") occluders, and devices other than occluders such as a CardioMEMS® HF System, may achieve similar benefits if the delivery process includes the use of an extended dilator like dilator 20.

Delivery devices for delivering occluders or other medical devices to or near the heart frequently include steering capabilities to further help navigate the tortuous delivery pathway and to increase the likelihood of achieving the best positions of the medical device relative to the patient anatomy. For example, delivery devices for delivering a patent ductus arteriosus PDA occluder and for delivering the CardioMEMS® HF System are typically steerable. The way in which steering of the delivery device is achieved typically is with the use of one or more steering rings fixed near a distal end of the sheath of the delivery device catheter, with one or more pull wires extending from the steering ring(s) to a control handle, the pull wires extending through one or more lumens formed in the wall of the delivery device sheath. Because a steerable delivery device sheath must be able to accommodate pull wire(s) and steering ring(s), the wall thickness of the delivery device sheath typically must be thicker compared to a similar delivery device sheath that lacks the steering capability. Furthermore, if a delivery device sheath has a maximum desired outer diameter, the available payload (e.g., size of the inner lumen of the sheath through which a medical device may be delivered) of a steerable delivery device sheath will be smaller than an otherwise identical non-steerable delivery device sheath, because the increased wall thickness for a given outer diameter results in a smaller inner diameter.

Dilators that are used with delivery devices, such as dilator D or extended dilator 20, typically have large wall thicknesses. The large wall thickness of dilators is a result of the dilators needing a small lumen to accept a guidewire but needing a relatively large outer diameter in order to securely fit within the inner lumen of the delivery device and to provide a smooth and atraumatic transition between the guidewire and the delivery device sheath. According to one aspect of the disclosure, a delivery device sheath may maintain a relatively large inner diameter (given a fixed outer diameter requirement) by removing the steering capability from the delivery device sheath, thus reducing the wall thickness of the delivery device sheath. At the same time, the system may maintain steering capability by moving the steering functionality to the dilator. As noted above, dilators typically have relatively large wall thicknesses, and thus may accommodate steering components such as steering ring(s) and pull wire(s) without requiring a change in the wall thickness of the dilator. In other words, by moving the steering capability to the dilator, the entire delivery system may maintain substantially identical overall functionality while increasing the payload capacity of the delivery device sheath.

Figure 9:
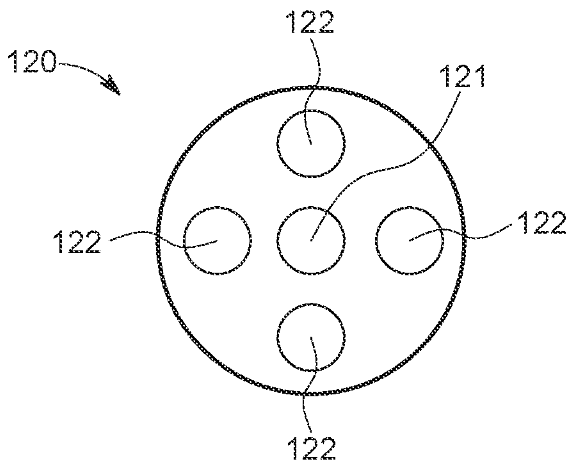
FIG. 9 is a transverse cross-section of a dilator according to an embodiment of the disclosure.
Figure 10:
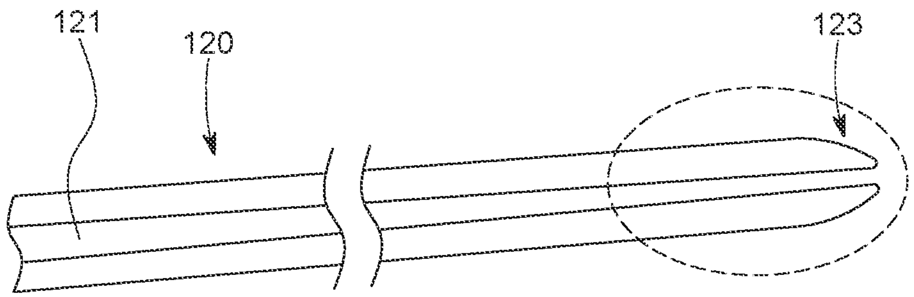
FIG. 10 is a longitudinal cross-section of the dilator of FIG. 9 in a first stage of manufacture.

FIG. 9 shows a transverse cross-section of one example of a steerable dilator 120 according to an aspect of the disclosure. In the illustrated embodiment, dilator 120 includes a central guidewire lumen 121 for accepting a guidewire (such as the guidewires GW described above) therethrough. As shown in FIG. 10, the guidewire lumen 121 may extend to a distal tip 123 of the dilator 120, so that the distal tip 123 of the dilator 120 may be passed over a proximal end of the guidewire GW. The distal tip 123 may be heat shaped to have an ogive, tapered or bullet shape. Referring back to FIG. 9, a plurality of peripheral steering lumens 122 may be provided radially outward of the guidewire lumen 121. In the illustrated embodiment, the dilator 120 includes four peripheral steering lumens 120 provided at 90-degree intervals, but it should be understood that more or fewer than four peripheral steering lumens 122 may be provided. Although it is not required, it is preferable that the peripheral steering lumens 122 are provided in pairs that are about 180 degrees offset from each other. As is described below, the peripheral steering lumens 122 may be sized and shaped to receive steering cables (e.g., pull wires) therethrough, with the distal ends of the peripheral steering lumens 122 opening to the portion of the dilator 120 where the steering ring(s) 125 are located.

Figure 11:
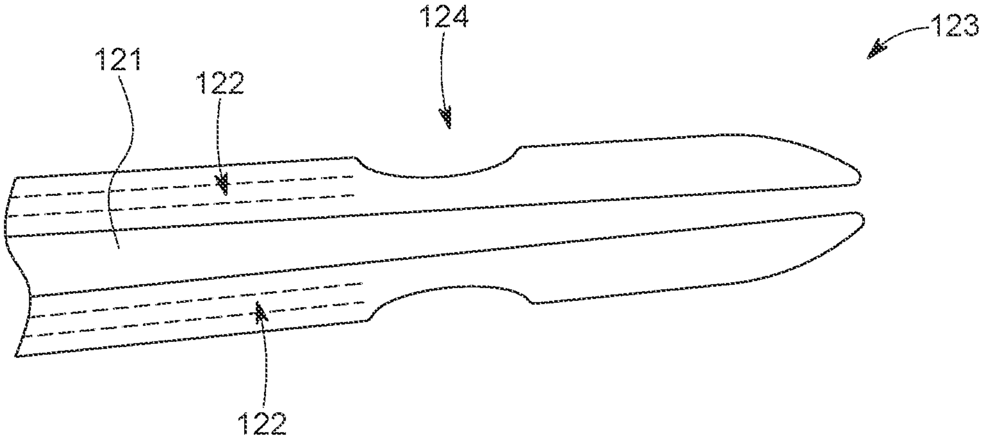
FIG. 11 is an enlarged view of the distal tip of the dilator of FIG. 10.
Figure 12:
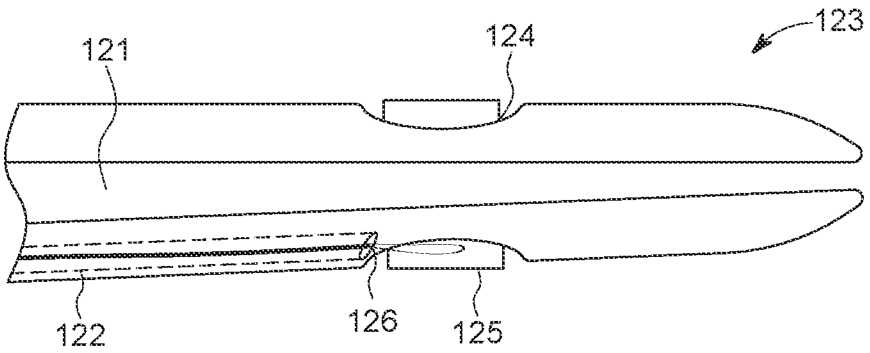
FIG. 12 is an enlarged longitudinal cross-section of the dilator of FIG. 9 in a second stage of manufacture.
Figure 13:
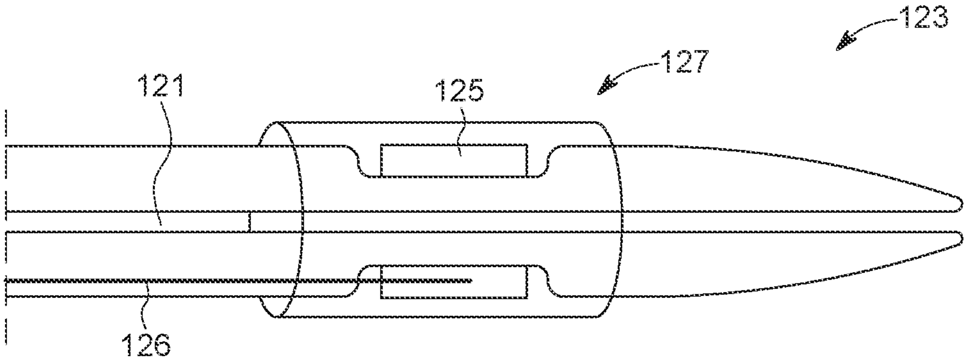
FIG. 13 is an enlarged longitudinal cross-section of the dilator of FIG. 9 in a third stage of manufacture.

FIG. 11 is an enlarged cross-section of the portion of the tip 123 of the dilator 120 in dashed lines in FIG. 10. A groove, recess, or detent 124 may be created in the tip 123 just distal to the distal ends of the peripheral steering lumens 122, slightly proximal to the distal-most end of the dilator 120. This detent 124 may be created via any suitable mechanism, including for example applying a compressive force and heat simultaneously. After forming the detent 124, a steering ring 125 may be positioned on the detent 124 and fixed to the dilator 120, for example via swaging, bonding (e.g., via adhesives), or any other suitable mechanism, as is shown in FIG. 12. If the distal ends of the peripheral steering lumens 122 are not already open to the steering ring 125, a port may be created to open the peripheral steering lumens 122 to the steering ring 125, and steering cables (or pull wires) 126 may be coupled to the steering ring 125 and routed through the peripheral steering lumens 122. To complete the assembly, as shown in FIG. 13, a thin-walled tube 127 may be positioned to overlay the steering ring 125 and extend slightly proximal to and distal to the ends of the detent 124. The thin-walled tube 127 may be heated or reflowed in order to create a smooth outer surface of the dilator 120 in the area of the pull ring 125 and the previously formed detent 124. With this smooth outer surface, the dilator 120 will not get caught on the inside of the delivery device 10 or the patient's anatomy as the dilator 120 translates relative to either.

Dilator 120 may be formed of any suitable material. In some embodiments, the dilator 120 may be formed of a generally soft material, such as low-density polyethylene ("LDPE"), polyethylene ("PE"), a urethane such as pelletized urethane offered by Lubrizol under the tradename Pellethane®, or a polyether block amide offered under the tradename PEBAX® having a durometer of, for example, 63D, 55D, or 45D, preferably with a lubricant in the PEBAX® such as the lubricant offered under the tradename Mobilize®. The entire dilator 120 may be formed of these types of material, or in other embodiments, the dilator 120 may be formed with zones having different stiffness. The below embodiment of dilator 220 is described as having multiple stiffness zones, but it should be understood that the embodiments of dilators described herein may have a substantially uniform stiffness throughout or formed with different stiffness zones.

Figure 14:
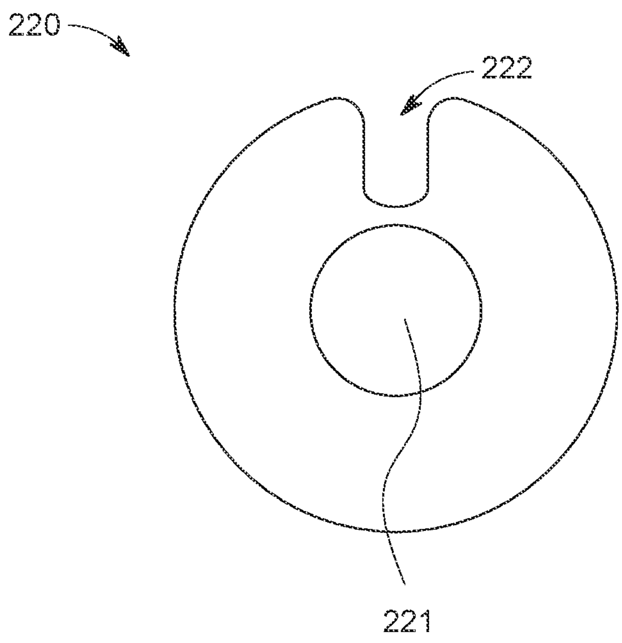
FIG. 14 is a transverse cross-section of a dilator according to another embodiment of the disclosure, in a first stage of manufacture.
Figure 15:
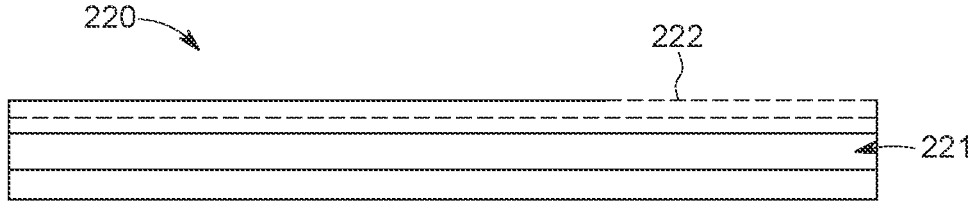
FIG. 15 is a longitudinal cross-section of the dilator of FIG. 14.
Figure 16:
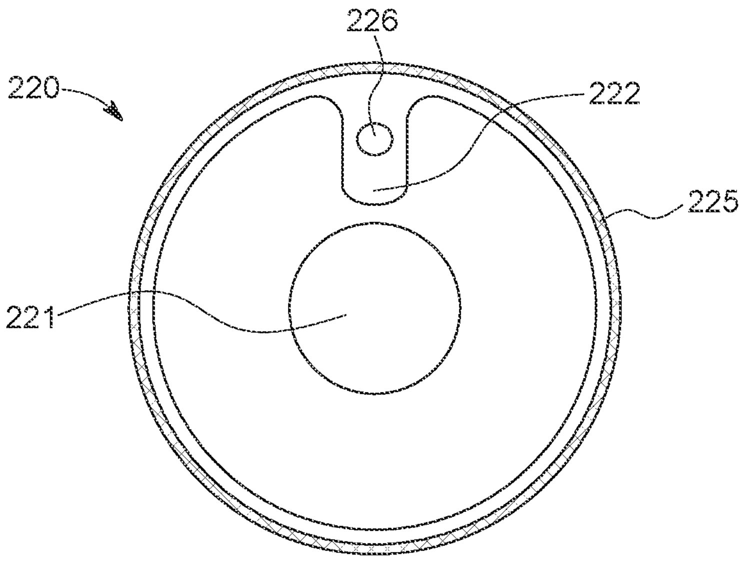
FIG. 16 is a transverse cross-section of the dilator of FIG. 14 in a second stage of manufacture.
Figure 17:
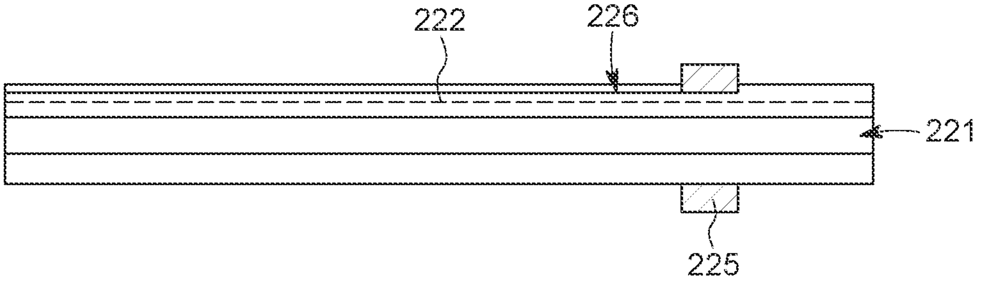
FIG. 17 is a longitudinal cross-section of the dilator of FIG. 16.

Instead of forming the dilator 120 as a multi-lumen tubing, FIGS. 14-18 illustrate an embodiment of dilator 220 formed as an assembly, in different stages of manufacture. FIGS. 14-15 are transverse and longitudinal cross-sections, respectively, of the dilator 220 in an initial stage of manufacture. In particular, FIGS. 14-15 show the base extrusion of the dilator 220, which may be a generally cylindrical member with a guidewire lumen 221 extending therethrough. In some embodiments, a channel, recess, or groove 222, which may be generally "U"- or "C"-shaped, may be formed extending longitudinally along an outer surface of the base extrusion. If the groove 222 is included, it may stop short of the distal end of the base extrusion, as best shown in FIG. 17 described below. In other embodiments, the groove 222 may be omitted. The base extrusion may be formed of any of the materials described above in connection with dilator 120. The guidewire lumen 221 may be sized for accepting a guidewire (such as the guidewires GW described above) therethrough, and the guidewire lumen 221 may extend to the distal end of the base extrusion at this stage of manufacture.

During a second stage of manufacture, a steering ring 225 may be positioned over the base extrusion near a distal end thereof. If a groove 222 is included, the steering ring 225 may be positioned at or adjacent the distal-most end of the groove 222. The steering ring 225 may be coupled to the base extrusion via any suitable mechanism, or instead may remain uncoupled, with the exterior jacket (described below) maintaining the steering ring 225 in place. A steering wire or pull wire 226 may be coupled to the steering ring 225, for example via welding, with the pull wire 226 extending through the groove 222. In some embodiments, multiple grooves may be provided, with pull wires positioned in each groove. In some embodiments, grooves may be omitted and the pull wire(s) 226 may sit on the outer surface of the base extrusion prior to the exterior jacket (described below) being created.

Figure 18:
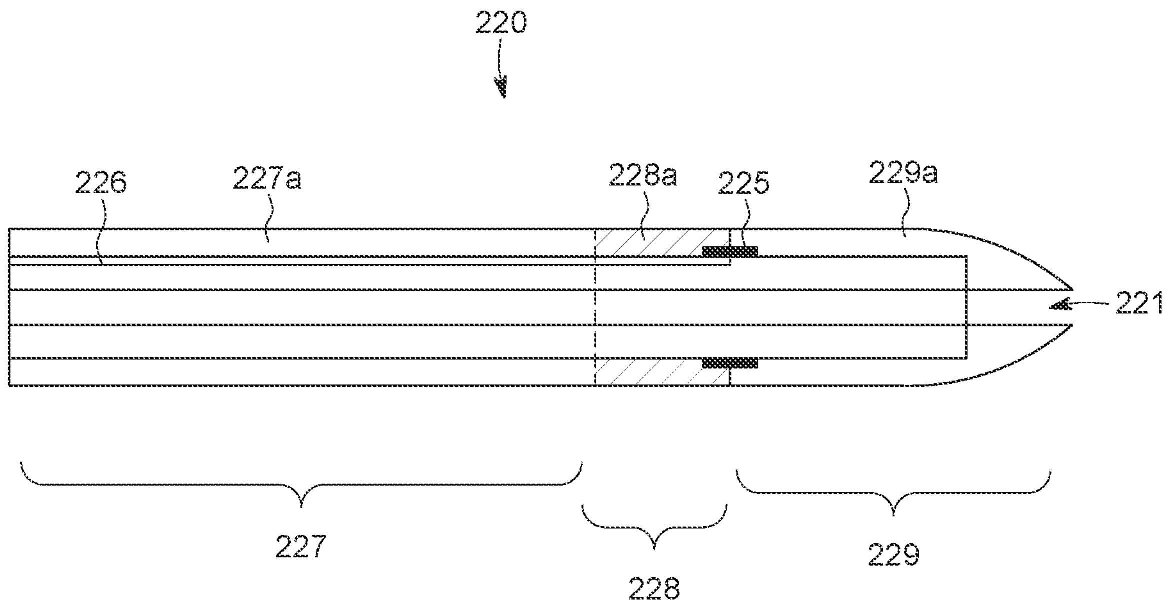
FIG. 18 is a longitudinal cross-section of the dilator of FIG. 16 in a third stage of manufacture.

In a final stage of manufacture, as shown in FIG. 18, an exterior jacket may be added over the base extrusion. The exterior jacket is not provided with a separate part number in FIG. 18 because, as will become clear below, the exterior jacket may be formed of multiple sections that in the aggregate form the exterior jacket. In one example, the exterior jacket may be formed by reflowing one or more polymers or similar materials over the base extrusion. By choosing different materials to form different sections of the exterior jacket, varying zones of stiffness may be created to provide the dilator 220 enough stiffness or column strength to be pushed along the vasculature, but enough flexibility, particularly at the tip area, to enhance the steerability of the dilator 220. For example, a proximal section **227*a* of the exterior jacket may be formed of a material having a relatively high stiffness or durometer, in order to create a high stiffness zone 227. The high stiffness zone 227 may extend from the proximal end of the catheter to a point at or adjacent to the steering ring 225. In some examples, the proximal section 227*a* may be formed of a material such as high-density polyethylene ("HDPE"), a polyether block amide (e.g., PEBAX®) having a durometer of 72D, or Nylon 11. Still referring to FIG. 18, a distal section 229*a* of the exterior jacket may be formed of a material having a relatively low stiffness or durometer to create a low stiffness zone 229. The low stiffness zone 229 may extend from a point at or adjacent to the steering ring 225 to the distal end of the dilator 220. If the distal section 229*a* extends beyond the distal end of the base extrusion, as shown in FIG. 18, it may form a tapered and/or atraumatic distal tip having an interior lumen that opens to, and/or is a continuation of, guidewire lumen 221. In some examples, the distal section 229*a* may be formed of a material such as LDPE, a polyether block amide (e.g., PEBAX®) having a durometer of 40D, 55D, or 63D, or Nylon 6. In some embodiments, a transition section 228*a* may be formed between the proximal section 227*a* and the distal section 229*a*. For example, the material forming the proximal section 227*a* and the distal section 229*a* may be mixed in the transition section 228*a* to form a medium stiffness zone 228. In the illustrated example, the transition section 228 is formed at and/or just proximal to the steering ring 225. However, in other embodiments, the transition section 228*a* may be omitted and instead, the transition section 228*a* may be formed of the same material as the proximal section 227*a* to extend the high stiffness zone 227 distally, or as the same material as the distal section 229*a* to extend the low stiffness zone 229 proximally. With the configurations described above, the relatively higher durometer, stiffer proximal portion of the dilator 220 will help a user to push the dilator 220 distally through the vasculature, while the relatively lower durometer, more flexible distal portion of the dilator 220 will help to allow the distal portion of the dilator 220 to deflect during steering of the dilator 220**.

Figure 19:
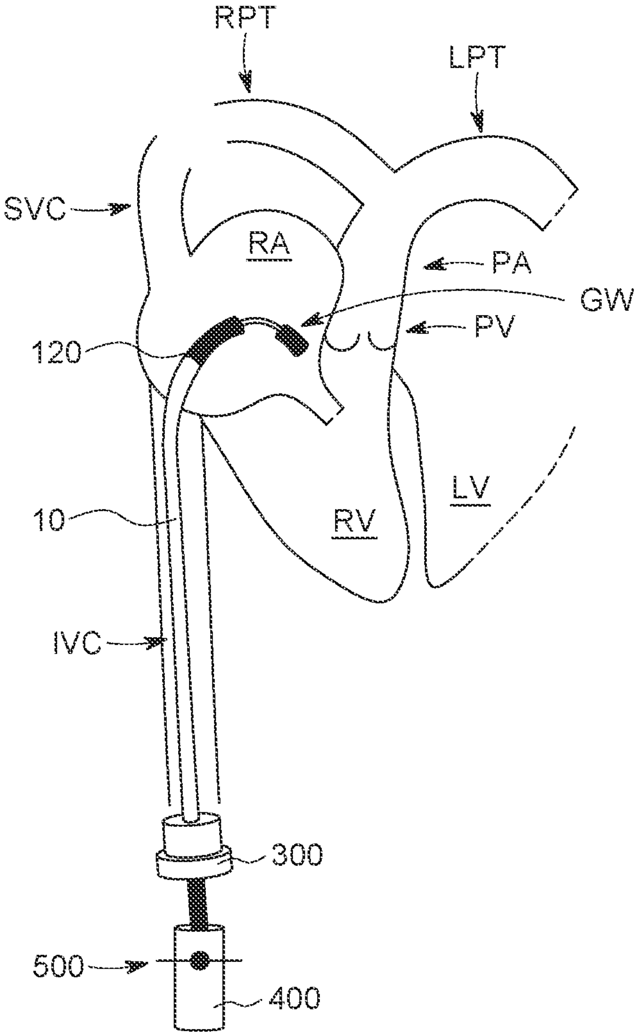
FIGS. 19-21 are schematic illustrations of the dilator of FIG. 13 or 18 at different stages of delivery to a left pulmonary trunk of a patient.
Figure 20:
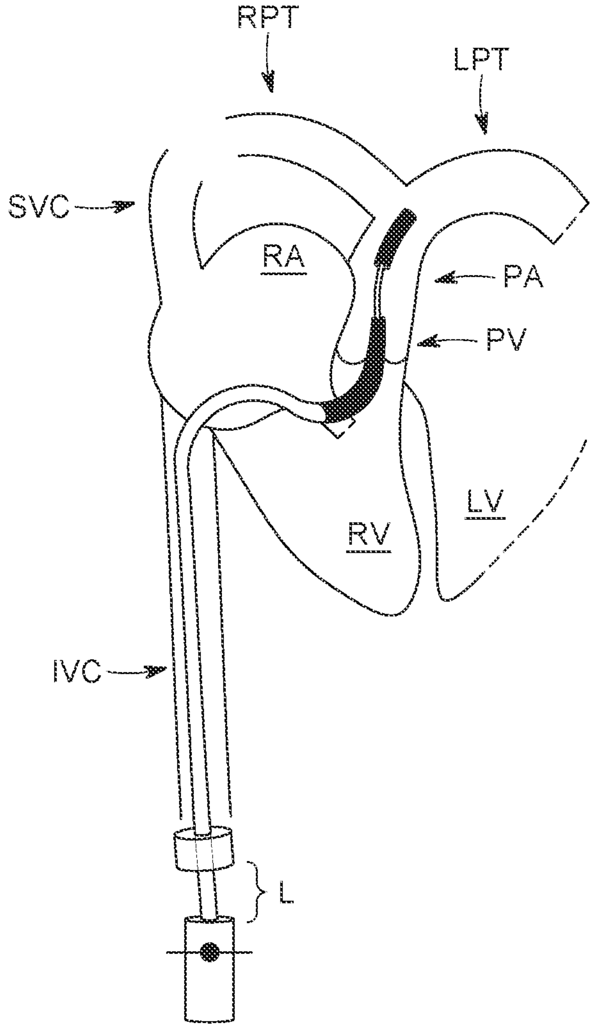
Figure 21:
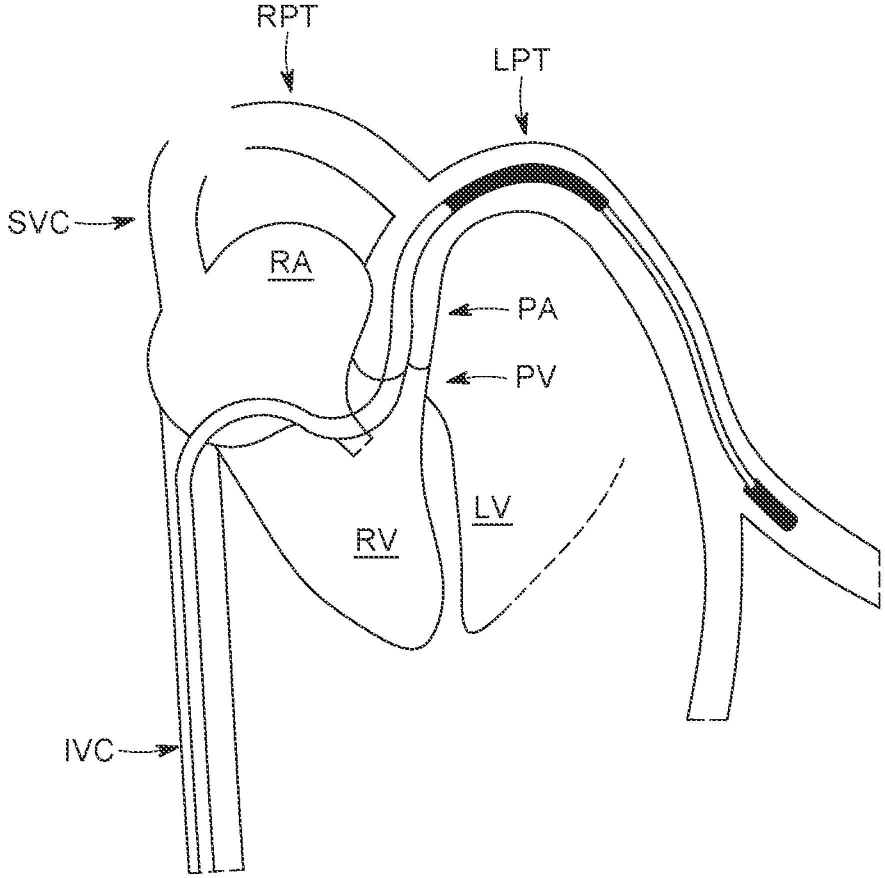

FIGS. 19-21 illustrate dilator 120 being used with delivery device 10 and guidewire GW to advance the delivery device 10 to the left pulmonary trunk LPT, for example, to deliver a CardioMEMS™ HF System. However, as should be understood from the above disclosure, the dilator 120 may be used to deliver other medical devices, including to other areas, such as to occlude a patent ductus arteriosus PDA. It should be further be understood that, although FIGS. 19-21 refer to dilator 120, the same concepts apply to the use of dilator 220. Further, the guidewire GW may be any suitable guidewire, for example including those described above.

Typically, dilators used to deliver medical devices to the right heart may only extend beyond the distal end of the delivery device 10 a minimal amount, including for example the distal tapered or atraumatic tip of the dilator and a landing zone of around 10 mm. However, steerable dilator 120 (or 220) may be longer than such typical dilators, for example by between about 2 cm and about 5 cm. This extra length of the dilator 120 may allow for the dilator 120 to translate relative to the distal end of the delivery device 10 so that the point of the dilator's steering (e.g., steering ring 125) can be positioned at different locations relative to the distal end of the delivery device 10. This may allow for the distal end of the dilator 120 to be deflected in the desired direction, and then the distal end of the delivery device 10 advanced relative to the deflected dilator tip to follow the bend or deflection of the dilator 120. This may further allow and aid in steering the guidewire GW into position without requiring any sheath exchanges.

In FIG. 19, the hub 400 of the dilator 120 is positioned outside the patient, with the dilator 120 extending through the hub 300 of the delivery device 10, which is also outside the patient. As can be seen in FIG. 20, a length L of the dilator 120 (e.g., between about 2 cm and about 5 cm) remains between the dilator hub 400 and the delivery device hub 300, allowing for an amount of translation between the delivery device 10 and the dilator 120. Referring again to FIG. 19, at this point in the delivery, the guidewire GW has been advanced to the right atrium RA, and the dilator 120 and delivery device 10 have been advanced over the guidewire GW, through the inferior vena cava IVC (which is opposite the superior vena cava SVC), and into the right atrium RA. At this point, the steering actuator 500 of the dilator 120 may be activated to deflect the tip of the dilator 120 toward the tricuspid valve and the right ventricle RV. The steering actuator 500 may take any suitable form, including known catheter steering mechanisms. An example of a steering actuator 500 is provided in connection with FIGS. 22-23. With the dilator 120 deflected toward the tricuspid valve and the right ventricle RV, the delivery device 10 may be advanced distally relative to the dilator 120 so that the delivery device 10 follows the deflected dilator 120 toward the right ventricle RV.

After the distal end of the delivery device 10 has crossed into (or begun to cross into) the right ventricle RV, the dilator 120 may be advanced relative to the delivery device and then steered or deflected again toward or through the pulmonary valve PV, as shown in FIG. 20. Again, the delivery device 10 may then be advanced distally relative to the dilator 120 so that the delivery device 10 follows the deflected dilator 120 until it crosses the pulmonary valve PV and into the pulmonary artery PA. After the distal end of the delivery device 10 has crossed (or begun to cross) the pulmonary valve PV, the dilator 120 may be advanced relative to the delivery device into the pulmonary artery PA and then steered toward the left pulmonary trunk LPT (or away from the right pulmonary trunk RPT), as shown in FIG. 21. The delivery device 10 may be advanced distally again relative to the dilator 120 until the delivery device 10 is positioned within the left pulmonary trunk LPT, which for this procedure is the intended target site for delivering the medical device. Once the delivery device 10 is at the target site, the dilator 120 may be removed from the patient by withdrawing it from the delivery device 10, and the medical device may then be passed through the sheath of the delivery device 10 to be implanted at the target site. It should be understood that, although FIGS. 19-21 illustrate a method for positioning the delivery device 10 within the left pulmonary trunk LPT, a substantially similar procedure may be performed, with different steering, to position the delivery device within or across a patent ductus arteriosus PDA or within the right pulmonary trunk RPT. Further, while the embodiments shown herein focus on right heart procedures, the embodiments may be used for left heart procedures with the aid of a transseptal puncture to allow the delivery device to cross from the right heart (e.g., the right atrium) to the left heart (e.g., the left atrium). Such procedures may include mitral valve leaflet repair or left atrial appendage occlusion.

Figure 22:
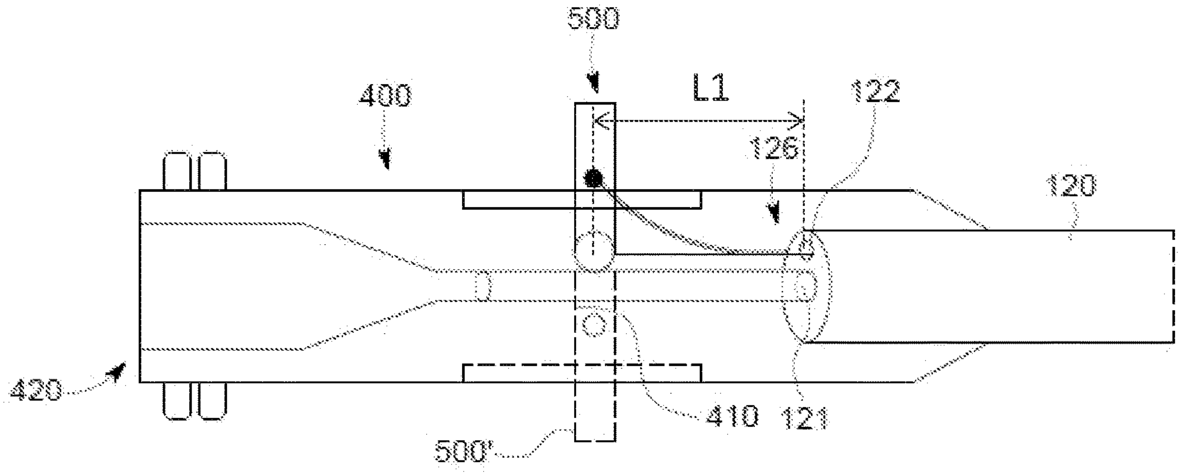
FIGS. 22-23 are schematic illustrations of a steering handle for use with the dilator of FIG. 13 or 18 in non-activated and activated states, respectively.
Figure 23:
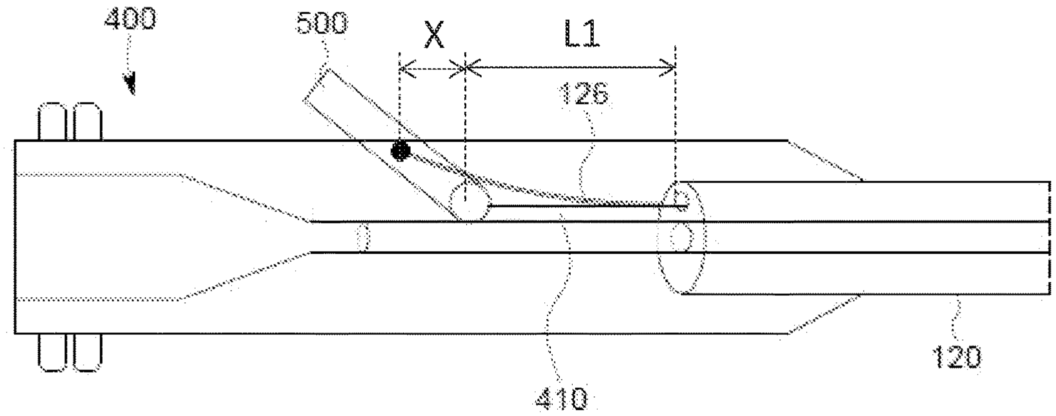

FIG. 22 shows a schematic illustration of the dilator hub 400 and steering actuator 500 that may be used with dilator 120 or 220, while in a non-actuated state. FIG. 22 shows the proximal end of the dilator 120 with a steering cable 126 extending proximally out of a peripheral steering lumen 122 (in this embodiment, dilator 120 includes only a single peripheral steering lumen 122). Tubing 410, such as polyimide tubing or a hypotube, may extend proximally from the guidewire lumen 121 to connect to the flush port 420 of the dilator hub 400. The tubing 410 may effectively serve as an extension of the guidewire lumen 121. The dilator hub 400 may include a steering actuator, for example in the form of a single lever 500, that extends generally perpendicular to the longitudinal axis of the hub 400. The single lever may be spaced a distance L1 from the proximal end of the dilator 120 where the steering cable 126 exits the peripheral steering lumen 122. The proximal end of the steering cable 126 (which may be a single wire or two ends of a wire which loops around the steering ring 125) may be coupled to the single lever 500, and the single lever 500 may be pivotably coupled to the dilator hub 400. As shown in FIG. 23, pulling the single lever 500 proximally pulls the steering cable 126 a distance X, so that the distance between the point of attachment of the steering cable 126 to the single lever 500 and the proximal end of the dilator 120 is a total distance L1+X. This activation of single lever 500 puts tension on the steering cable 126, pulling on the steering ring 125 and deflecting the distal end of the dilator 120. Referring briefly back to FIG. 22, the single lever 500 may instead be provided as a double lever 500, 500'. It should be understood that, although one particular steering handle or mechanism 500 is illustrated in connection with FIGS. 21-22, various other types of steering handles and mechanisms may be used to achieve the desired steering, including traditional steering mechanisms (e.g., rotating knobs) known in the art.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of manufacturing a dilator for use with a delivery catheter, the method comprising:

forming the dilator to have a cylindrical base, a central guidewire lumen extending through the cylindrical base, and a tapered tip;

positioning a steering ring over a distal end portion of the cylindrical base, the steering ring having at least one steering cable coupled thereto;

after positioning the steering ring, forming an exterior jacket over the cylindrical base so that the exterior jacket has a proximal portion formed of a first material and a distal portion formed of a second material different than the first material, the proximal portion being stiffer than the distal portion.

2. The method of claim 1, wherein the proximal portion is positioned proximal to the steering ring, and the distal portion is positioned distal to the steering ring.

3. The method of claim 1, wherein the proximal portion directly transitions to the distal portion.

4. The method of claim 1, wherein forming the exterior jacket includes forming an intermediate portion between the proximal portion and the distal portion, the intermediate portion being formed of both the first material and the second material so that the intermediate portion is stiffer than the distal portion, and the proximal portion is stiffer than the intermediate portion.

5. The method of claim 1, wherein the cylindrical base, upon being formed, includes a channel extending longitudinally along an outer surface of the cylindrical base.

6. The method of claim 5, wherein positioning the steering ring over the distal end portion of the cylindrical base includes positioning the steering ring at a distal end of the channel so that the at least one steering cable extends along the channel.

7. The method of claim 5, wherein the channel is "U"-shaped or "C"-shaped.

8. The method of claim 1, wherein the steering ring has an annular shape defining an open interior space, the cylindrical base of the dilator extending through the open interior space of the steering ring.

9. The method of claim 1, wherein the at least one steering cable has a first end and a second end opposite the first end, the second end being coupled to the steering ring, the first end being coupled to a steering actuator.

10. The method of claim 9, wherein the steering actuator is a steering knob.

11. The method of claim 1, wherein the exterior jacket is formed over the cylindrical base by reflowing one or more materials over the cylindrical base.

12. The method of claim 11, wherein the one or more materials are polymers.

13. The method of claim 1, wherein the first material is a high density polyethylene ("HDPE").

14. The method of claim 1, wherein the first material is a polyether block amide having a durometer of 72D.

15. The method of claim 1, wherein the second material is formed of a low density polyethylene ("LDPE").

16. The method of claim 1, wherein the second material is a polyether block amide having a durometer of 40D, 55D, or 63D.

* * * * *